(12) United States Patent
Michelson

(10) Patent No.: US 8,409,292 B2
(45) Date of Patent: *Apr. 2, 2013

(54) SPINAL FUSION IMPLANT

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/109,791

(22) Filed: May 17, 2011

(65) Prior Publication Data

US 2011/0224795 A1   Sep. 15, 2011

Related U.S. Application Data

(63) Continuation of application No. 12/798,364, filed on Apr. 3, 2010, now Pat. No. 7,942,933, which is a continuation of application No. 11/085,706, filed on Mar. 19, 2005, now Pat. No. 7,691,148, which is a continuation of application No. 08/484,928, filed on Jun. 7, 1995, now Pat. No. 6,923,810.

(51) Int. Cl.
*A61F 2/44* (2006.01)

(52) U.S. Cl. ..................... 623/17.16; 606/246

(58) Field of Classification Search ............... 623/17.11, 623/17.16; 606/246
See application file for complete search history.

(56) References Cited

U.S. PATENT DOCUMENTS

| | | | |
|---|---|---|---|
| 350,420 A | 10/1886 | Dillon | |
| 1,137,585 A | 4/1915 | Craig | |
| 2,065,659 A | 12/1936 | Cullen | |
| 2,181,746 A | 11/1939 | Siebrandt | |
| 2,243,718 A | 5/1941 | Moreira | |
| 2,372,622 A | 3/1945 | Wormell | |
| 2,514,665 A | 7/1950 | Myller | |
| 2,537,070 A | 1/1951 | Longfellow | |
| 2,543,780 A | 3/1951 | Hipps et al. | |
| 2,677,369 A | 5/1954 | Knowles | |
| 2,774,350 A | 12/1956 | Cleveland | |
| 2,789,558 A | 4/1957 | Rush | |
| 2,832,343 A | 4/1958 | Mose | |
| 2,842,131 A | 7/1958 | Smith | |
| 2,878,809 A | 3/1959 | Treace | |

(Continued)

FOREIGN PATENT DOCUMENTS

| | | |
|---|---|---|
| CA | 1 328 957 | 5/1994 |
| CA | 2 151 481 | 3/1995 |

(Continued)

OTHER PUBLICATIONS

Albrektsson, T., et al.; Osseointegrated Titanium Implants; Acta. Orthop. Scand.; vol. 52:155-170 (1981).

(Continued)

*Primary Examiner* — Ellen C Hammond
(74) *Attorney, Agent, or Firm* — Martin & Ferraro, LLP

(57) ABSTRACT

The present invention is directed to a variety of interbody spinal fusion implants for insertion across the surgically corrected height of a disc space between two adjacent vertebral bodies of a human spine. The spinal fusion implants of the present invention have opposed upper and lower portions with openings extending through the implant to provide for bone growth from vertebral body to vertebral body. The upper and lower portions of the spinal fusion implants of the present invention have bone engaging projections to engage the implants to the adjacent vertebral bodies.

20 Claims, 5 Drawing Sheets

U.S. PATENT DOCUMENTS

| | | | |
|---|---|---|---|
| 3,128,768 A | 4/1964 | Geistauts |
| 3,298,372 A | 1/1967 | Feinberg |
| 3,426,364 A | 2/1969 | Lumb |
| 3,486,505 A | 12/1969 | Morrison |
| 3,604,487 A | 9/1971 | Gilbert |
| 3,605,123 A | 9/1971 | Hahn |
| 3,618,611 A | 11/1971 | Urban |
| 3,709,219 A | 1/1973 | Halloran |
| 3,719,186 A | 3/1973 | Merig, Jr. |
| 3,720,959 A | 3/1973 | Hahn |
| 3,750,652 A | 8/1973 | Sherwin |
| 3,848,601 A | 11/1974 | Ma et al. |
| 3,855,638 A | 12/1974 | Pilliar |
| 3,867,728 A | 2/1975 | Stubstad et al. |
| 3,867,950 A | 2/1975 | Fischell |
| 3,875,595 A | 4/1975 | Froning |
| 3,888,260 A | 6/1975 | Fischell |
| 3,892,232 A | 7/1975 | Neufeld |
| 3,905,047 A | 9/1975 | Long |
| 3,906,550 A | 9/1975 | Rostoker et al. |
| 3,915,151 A | 10/1975 | Kraus |
| 3,916,907 A | 11/1975 | Peterson |
| 3,918,440 A | 11/1975 | Kraus |
| 3,942,535 A | 3/1976 | Schulman |
| 3,948,262 A | 4/1976 | Zaffaroni |
| 3,952,334 A | 4/1976 | Bokros et al. |
| 3,987,499 A | 10/1976 | Scharbach et al. |
| 4,016,651 A | 4/1977 | Kawahara et al. |
| 4,027,392 A | 6/1977 | Sawyer et al. |
| D245,259 S | 8/1977 | Shen |
| 4,051,905 A | 10/1977 | Kleine |
| 4,059,115 A | 11/1977 | Jumashev et al. |
| 4,070,514 A | 1/1978 | Eatherly et al. |
| 4,082,097 A | 4/1978 | Mann et al. |
| 4,086,701 A | 5/1978 | Kawahara et al. |
| 4,124,026 A | 11/1978 | Berner et al. |
| 4,142,517 A | 3/1979 | Stavropoulos et al. |
| 4,168,326 A | 9/1979 | Broemer et al. |
| 4,175,555 A | 11/1979 | Herbert |
| 4,177,524 A | 12/1979 | Grell et al. |
| 4,181,457 A | 1/1980 | Holmes |
| 4,197,850 A | 4/1980 | Schulman et al. |
| 4,206,516 A | 6/1980 | Pilliar |
| 4,222,128 A | 9/1980 | Tomonaga et al. |
| D257,511 S | 11/1980 | Zahn |
| 4,232,679 A | 11/1980 | Schulman |
| 4,237,948 A | 12/1980 | Jones et al. |
| 4,258,716 A | 3/1981 | Sutherland |
| 4,259,072 A | 3/1981 | Hirabayashi et al. |
| 4,262,369 A | 4/1981 | Roux |
| 4,271,832 A | 6/1981 | Evans et al. |
| D260,525 S | 9/1981 | Lassiter |
| 4,289,123 A | 9/1981 | Dunn |
| 4,293,962 A | 10/1981 | Fuson |
| 4,309,777 A | 1/1982 | Patil |
| 4,328,593 A | 5/1982 | Sutter et al. |
| 4,333,469 A | 6/1982 | Jeffcoat et al. |
| 4,341,206 A | 7/1982 | Perrett et al. |
| 4,349,921 A | 9/1982 | Kuntz |
| 4,356,572 A | 11/1982 | Guillemin et al. |
| 4,401,112 A | 8/1983 | Rezaian |
| 4,405,319 A | 9/1983 | Cosentino |
| 4,414,979 A | 11/1983 | Hirshorn et al. |
| 4,423,721 A | 1/1984 | Otte et al. |
| 4,439,152 A | 3/1984 | Small |
| 4,450,834 A | 5/1984 | Fischer |
| 4,481,943 A | 11/1984 | Michelson |
| 4,484,570 A | 11/1984 | Sutter et al. |
| 4,492,226 A | 1/1985 | Belykh et al. |
| 4,497,320 A | 2/1985 | Nicholson et al. |
| 4,501,269 A | 2/1985 | Bagby |
| 4,507,115 A | 3/1985 | Kambara et al. |
| RE31,865 E | 4/1985 | Roux |
| 4,530,360 A | 7/1985 | Duarte |
| 4,535,374 A | 8/1985 | Anderson et al. |
| 4,535,485 A | 8/1985 | Ashman et al. |
| 4,542,539 A | 9/1985 | Rowe, Jr. et al. |
| 4,545,374 A | 10/1985 | Jacobson |
| 4,547,390 A | 10/1985 | Ashman et al. |
| 4,549,547 A | 10/1985 | Brighton et al. |
| 4,552,200 A | 11/1985 | Sinha et al. |
| 4,553,273 A | 11/1985 | Wu |
| 4,554,914 A | 11/1985 | Kapp et al. |
| D281,814 S | 12/1985 | Pratt et al. |
| 4,570,623 A | 2/1986 | Ellison et al. |
| 4,570,624 A | 2/1986 | Wu |
| 4,592,346 A | 6/1986 | Jurgutis |
| 4,599,086 A | 7/1986 | Doty |
| 4,600,000 A | 7/1986 | Edwards |
| 4,602,638 A | 7/1986 | Adams |
| 4,604,995 A | 8/1986 | Stephens |
| 4,608,052 A | 8/1986 | Van Kampen et al. |
| 4,611,581 A | 9/1986 | Steffee |
| 4,619,264 A | 10/1986 | Singh |
| 4,628,921 A | 12/1986 | Rousso |
| 4,634,720 A | 1/1987 | Dorman et al. |
| 4,636,217 A | 1/1987 | Ogilvie et al. |
| 4,636,526 A | 1/1987 | Dorman et al. |
| 4,645,503 A | 2/1987 | Lin et al. |
| 4,653,486 A | 3/1987 | Coker |
| 4,655,777 A | 4/1987 | Dunn |
| 4,661,536 A | 4/1987 | Dorman et al. |
| 4,664,567 A | 5/1987 | Edwards |
| 4,665,920 A | 5/1987 | Campbell |
| 4,677,883 A | 7/1987 | Lee |
| 4,677,972 A | 7/1987 | Tornier |
| 4,693,721 A | 9/1987 | Ducheyne |
| 4,696,290 A | 9/1987 | Steffee |
| 4,698,375 A | 10/1987 | Dorman et al. |
| 4,710,075 A | 12/1987 | Davison |
| 4,713,004 A | 12/1987 | Linkow et al. |
| 4,714,469 A | 12/1987 | Kenna |
| 4,721,103 A | 1/1988 | Freedland |
| 4,736,738 A | 4/1988 | Lipovsek et al. |
| 4,743,256 A | 5/1988 | Brantigan |
| 4,743,260 A | 5/1988 | Burton |
| 4,759,766 A | 7/1988 | Buettner-Janz et al. |
| 4,759,769 A | 7/1988 | Hedman et al. |
| 4,769,881 A | 9/1988 | Pedigo et al. |
| 4,781,591 A | 11/1988 | Allen |
| 4,790,303 A | 12/1988 | Steffee |
| 4,805,602 A | 2/1989 | Puno et al. |
| 4,820,305 A | 4/1989 | Harms et al. |
| 4,830,000 A | 5/1989 | Shutt |
| 4,834,757 A | 5/1989 | Brantigan |
| 4,848,327 A | 7/1989 | Perdue |
| 4,851,008 A | 7/1989 | Johnson |
| 4,863,476 A | 9/1989 | Shepperd |
| 4,863,477 A | 9/1989 | Monson |
| 4,865,603 A | 9/1989 | Noiles |
| 4,877,020 A | 10/1989 | Vich |
| 4,878,915 A | 11/1989 | Brantigan |
| 4,903,882 A | 2/1990 | Long |
| 4,904,260 A | 2/1990 | Ray et al. |
| 4,904,261 A | 2/1990 | Dove et al. |
| 4,911,718 S | 3/1990 | Lee et al. |
| 4,913,144 A | 4/1990 | Del Medico |
| 4,936,848 A | 6/1990 | Bagby |
| 4,943,291 A | 7/1990 | Tanguy |
| 4,950,296 A | 8/1990 | McIntyre |
| 4,955,885 A | 9/1990 | Meyers |
| 4,955,908 A | 9/1990 | Frey et al. |
| 4,957,495 A | 9/1990 | Kluger |
| 4,960,420 A | 10/1990 | Goble et al. |
| 4,961,740 A | 10/1990 | Ray et al. |
| 4,968,316 A | 11/1990 | Hergenroeder |
| 4,969,888 A | 11/1990 | Scholten et al. |
| 4,987,904 A | 1/1991 | Wilson |
| 5,015,247 A | 5/1991 | Michelson |
| 5,015,255 A | 5/1991 | Kuslich |
| 5,026,373 A | 6/1991 | Ray et al. |
| 5,030,236 A | 7/1991 | Dean |
| 5,055,104 A | 10/1991 | Ray |
| 5,059,193 A | 10/1991 | Kuslich |
| 5,062,845 A | 11/1991 | Kuslich et al. |
| 5,071,437 A | 12/1991 | Steffee |
| 5,084,050 A | 1/1992 | Draenert |

| | | | |
|---|---|---|---|
| 5,102,414 A | 4/1992 | Kirsch | |
| 5,108,422 A | 4/1992 | Green et al. | |
| 5,112,336 A | 5/1992 | Krevolin et al. | |
| 5,116,304 A | 5/1992 | Cadwell | |
| 5,122,130 A | 6/1992 | Keller | |
| 5,123,926 A | 6/1992 | Pisharodi | |
| 5,171,278 A | 12/1992 | Pisharodi | |
| 5,192,327 A | 3/1993 | Brantigan | |
| 5,246,458 A | 9/1993 | Graham | |
| 5,258,031 A | 11/1993 | Salib et al. | |
| 5,263,953 A | 11/1993 | Bagby | |
| 5,273,964 A | 12/1993 | Lemons | |
| 5,279,292 A | 1/1994 | Baumann et al. | |
| 5,292,252 A | 3/1994 | Nickerson et al. | |
| 5,306,309 A | 4/1994 | Wagner et al. | |
| 5,314,427 A | 5/1994 | Goble et al. | |
| 5,324,295 A | 6/1994 | Shapiro | |
| 5,352,229 A | 10/1994 | Goble et al. | |
| 5,360,430 A | 11/1994 | Lin | |
| 5,364,399 A | 11/1994 | Lowery et al. | |
| 5,370,662 A | 12/1994 | Stone et al. | |
| 5,370,697 A | 12/1994 | Baumgartner | |
| 5,393,036 A | 2/1995 | Sheridan | |
| RE34,871 E | 3/1995 | McGuire et al. | |
| 5,396,880 A | 3/1995 | Kagan et al. | |
| 5,397,359 A | 3/1995 | Mittelmeier et al. | |
| 5,397,364 A | 3/1995 | Kozak et al. | |
| 5,425,772 A | 6/1995 | Brantigan | |
| 5,435,723 A | 7/1995 | O'Brien | |
| 5,443,514 A | 8/1995 | Steffee | |
| 5,458,638 A | 10/1995 | Kuslich et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,571,109 A | 11/1996 | Bertagnoli | |
| 5,593,409 A | 1/1997 | Michelson | |
| 5,669,909 A | 9/1997 | Zdeblick et al. | |
| 5,683,463 A | 11/1997 | Godefroy et al. | |
| 5,766,252 A | 6/1998 | Henry et al. | |
| D397,439 S | 8/1998 | Koros et al. | |
| 5,876,457 A | 3/1999 | Picha et al. | |
| 5,906,616 A | 5/1999 | Pavlov et al. | |
| 6,923,810 B1 | 8/2005 | Michelson | |
| 7,691,148 B2 | 4/2010 | Michelson | |
| 7,942,933 B2 | 5/2011 | Michelson | |
| 2005/0165489 A1 | 7/2005 | Michelson | |

FOREIGN PATENT DOCUMENTS

| | | |
|---|---|---|
| DE | 1 961 531 | 7/1970 |
| DE | 24 46 039 | 4/1975 |
| DE | 29 10 627 | 9/1980 |
| DE | 31 01 333 A1 | 12/1981 |
| DE | 31 32 520 A1 | 6/1982 |
| DE | 35 05 567 A1 | 6/1986 |
| DE | 36 08 163 A1 | 9/1987 |
| DE | 36 20 549 | 12/1987 |
| DE | 43 02 397 A1 | 7/1993 |
| EP | 0 077 159 | 4/1983 |
| EP | 0 162 005 | 11/1985 |
| EP | 0 179 695 | 4/1986 |
| EP | 0 260 044 | 8/1988 |
| EP | 0 307 241 | 3/1989 |
| EP | 0 493 698 A1 | 7/1992 |
| EP | 0 499 465 A1 | 8/1992 |
| EP | 0 526 682 A1 | 2/1993 |
| EP | 0 551 187 A1 | 7/1993 |
| EP | 0 577 179 A1 | 1/1994 |
| EP | 0 599 419 A2 | 6/1994 |
| EP | 0 637 439 | 2/1995 |
| EP | 0 637 440 | 2/1995 |
| EP | 0 646 366 | 4/1995 |
| EP | 0 732 093 A2 | 9/1996 |
| ES | 283078 | 5/1985 |
| FR | 2 295 729 | 7/1976 |
| FR | 2 581 336 | 11/1986 |
| FR | 2 703 580 | 10/1994 |
| GB | 1291470 | 10/1972 |
| GB | 1492990 | 11/1977 |
| GB | 1531487 | 11/1978 |
| GB | 2076657 A | 12/1981 |
| GB | 2126094 A | 3/1984 |
| GB | 2164277 A | 3/1986 |
| JP | 60-31706 | 2/1985 |
| JP | 60-43984 | 3/1985 |
| JP | 62-155846 | 7/1987 |
| SE | 106 101 | 7/1939 |
| SU | 1107854 | 8/1984 |
| SU | 1124960 | 11/1984 |
| SU | 1217374 | 3/1986 |
| SU | 1222254 | 4/1986 |
| WO | WO 84/01298 | 4/1984 |
| WO | WO 91/06266 | 5/1991 |
| WO | WO 92/14423 | 9/1992 |
| WO | WO 93/01771 | 2/1993 |

OTHER PUBLICATIONS

Bagby, G.W.; Arthrodesis by the Distraction-Compression Method Using a Stainless Steel Implant; Orthopedics, vol. II, No. 6, pp. 931-934 (Jun. 1987).

Bagby, G.W.; Basket Implant Facilitates Spinal Fusion; Orthopedics Today, vol. 7, No. 10, (Oct. 1987).

Bagby, George W.; Wobbler Syndrome in Horses (the Ataxic Horse); Spokane County Medical Society Bulletin; Spring 1979.

Brandt, L, et al.; A Dowel Inserter for Anterior Cervical Interbody Fusion; J. Neurosurg. 61:793-794 (Oct. 1984).

Bullough, Peter G.; Atlas of Spinal Diseases; Figure 5.7; J.B. Lippincott Company; 1988.

Butts, M.K.; Biomechanical Analysis of a New Method for Spinal Interbody Fixation; 1987 Symposium, American Society of Mechanical Engineers, "Advance in Bioengineering", Boston, MA (Dec. 13-18, 1987).

Crawley et al.; A Modified Cloward's Technique for Arthrodesis of the Normal Metacarpophalangeal Joint in the Horse; Veterinary Surgery, vol. 17, No. 3, pp. 117-127 (1988).

Crock, H.V.; "Anterior Lumbar Interbody Fusion Indications for its Used and Notes on Surgical Technique:" *Clinical Orthopedics*; vol. 165, pp. 157-163; May 1982.

Crock, H. V.; Practice of Spinal Surgery; Springer-Verlag/Wien, New York (1983).

Danek Group, Inc.; Spine Basics, Glossary (1993).

DeBowes, R.M., et al.; Study of Bovine . . . Steel Baskets; Transactions of the 29th Annual Meeting; Orthopaedic Research Society, vol. 8, p. 407, Mar. 8-10, 1983.

European Search Report dated Aug. 4, 1999 for European Patent Application No. 96917084 in the name of Gary Karlin Michelson.

Gillingham, F.J., et al.; Automatic Patient Monitoring in the Ward; Brit. J. Surg., vol. 53, No. 10, pp. 864-866 (Oct. 1966).

Gillingham, F.J., et al.; Head injuries; Proceedings of the 18th World Congress of the International College of Surgeons, Rome, pp. 68-71 (May 28-31, 1972).

Goldthwaite, N., et al.; Toward Percutaneous Spine Fusion; Ch. 45; Lumbar Spine Surgery; C.V. Mosby Company, pp. 512-522 (1987).

Harmon, Paul H.; Anterior Excision and Vertebral Body Fusion Operation for Intervertebral Disk Syndromes of the Lower Lumbar Spine: Three- to Five-Year Results in 244 Cases; pp. 107-127; Clinical Orthopaedics and Related Research, No. 26, J.B. Lippincott, 1963.

Harmon, Paul H.; A Simplified Surgical Technic for Anterior Lumbar Diskectomy and Fusion; Avoidance of Complications; Anatomy of the Retroperitoneal Veins; pp. 130-143; Clinical Orthopaedics and Related Research, No. 37, J.B. Lippincott Company, 1964.

Harris, P., et al.; Spinal Deformity After Spinal Cord Injury; Paraplegia, vol. 6, No. 4, pp. 232-238 (Feb. 1969).

Heim, Urs; Small Fragment Set Manual: Technique Recommended by the ASIF-Group; pp. 5-7, 10, 20, 21, 30; Springer-Verlag; 1974.

Hierholzer, G.; Manual on the AO/ASIF Tubular External Fixator; pp. 85-91; Springer-Verlag; 1985.

Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine, vol. 13, No. 3, pp. 363-365 (Mar. 1988).

Lin, Paul M.; Lumbar Interbody Fusion: Principles and Techniques in Spine Surgery; Techniques and Complications; pp. 81, 98, 120, 146, 173, 180-184, 204, 224, 225, 231; Aspen Publishers, Inc.; 1989.

Lumbar Spine Surgery, Techniques and Complications; History of Lumbar Spine Surgery (1994); pp. 11-15, 27, 30, 35-45, 265-268.

Maloney, A.F.J., et al.; Clinical and Pathological Observations in Fatal Head Injuries, Brit. J. Surg., vol. 56, No. 1, pp. 23-31 (Jan. 1969).

Morscher, E., et al.; Die vordere Verplattung der Halswirbelsäule mit dem Hohlschrauben-Plattensystem aus Titanium, Der Chirurg, vol. 57, pp. 702-707 (1986) with English Translation.

Muller, M.E.; Manual of Internal Fixation: Techniques Recommended by the AO Group; Second Edition, Expanded and Revised; pp. 3-20, 27-41, 53-58, 71-78, 94, 311, 320; Springer-Verlag; 1979.

Mylonas, C., et al.; Anterior Cervical Decompression and Fusion Using the Coventry Cervical Spreader and Dowel Inserter; British Journal of Neurosurgery, 7:545-549 (1993).

O'Neill, P., et al.; Spinal Meningoceles in Association with Neurofibromatosis; Neurosurgery, vol. 13, No. 1, pp. 82-84 (Jul. 1983).

Otero-Vich, Jose M.; Anterior Cervical Interbody Fusion with Threaded Cylindrical Bone; pp. 750-753; Journal of Neurosurgery, Nov. 1985, vol. 63, No. 5.

Rathke, F.W., et al.; Surgery of the Spine; Atlas of Orthopaedic Operations, vol. 1, p. 137, W.B. Saunders Co., Philadelphia (1979).

Raveh, J., et al.; Neue Rekonstruktionsmoglichkeiten des Unterkiefers bei knochernen Defekten nach Tumorresektionen; Der Chirurg vol. 53:459-467 (1982).

Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 (Aug. 1987).

Raveh, J., et al.; Use of the Titanium-coated Hollow Screw and Reconstruction Plate System in Bridging of Lower Jaw Defects; J. Oral Maxillofac Surg. 42:281-294 (1984).

Schmitz et al.; Performance of Alloplastic Materials and Design of an Artificial Disc; The Artificial Disc, Brock, Mayer, Weigel; pp. 23-34 (1991).

Tan, S.B.; A Modified Technique of Anterior Lumbar Fusion with Femoral Cortical Allograft; pp. 83-93; The Journal of Orthopaedic Surgical Techniques, vol. 5, No. 3, 1990.

Tech. Mitt. Krupp, Nickel-Titanium Spacers for Partial Stiffening of the Spinal Column—Problems Involved, Manufacture, Pretesting, and Clinical Use; vol. 42 (1984), No. 1, pp. 24-38; including translation pp. 5-27.

Thieme; Fusion of the Lumbar Spine; Anterior Monosegmental Fusion L5-S1; Atlas of Spinal Operations, pp. 270-274 (1993).

The SpF-T Spinal Fusion Stimulator: An Efficacious Adjunct that Meets the Diverse Needs of Spine Patients; EBI Medical Systems; (Aug. 1991).

The Use of Direct Current for Electrically Induced Osteogenesis; The Positive Effect of an Electronegative charge on Bone Growth; EBI Medical Systems (Feb. 1993).

Whatmore, W. J.; Meningioma Following Trauma; Brit. J. Surg., vol. 60, No. 6, pp. 496-498 (Jun. 1973).

Whatmore, W. J.; Proceedings of the Society of British Neurological Surgeons; Journal of Neurology, Neurosurgery, and Psychiatry, 50:1093-1100 (1987).

Whatmore, W. J.; Sincipital Encephalomeningaceles; Brit. J. Surg., vol. 60, No. 4, pp. 261-270 (Apr. 1973).

Whatmore, W.J., et al.; The Coventry Cervical Spreader and Dowel Inserter; ACTA Neurochirurgica, vol. 70, FASC. 1-2 (1984).

Wilterberger, B.R., Abbott, K.H.; "Dowel Intervertebral Fusion as Used in Lumbar Disc Surgery;" *The Journal of Bone and Joint Surgery*, vol. 39A, cover page and pp. 284-292 and 331; Apr. 1957.

Zindrick, et al.; Lumbar Spine Fusion: Different Types and Indications; The Lumbar Spine, vol. 1, Second Edition, pp. 588-593 (1996).

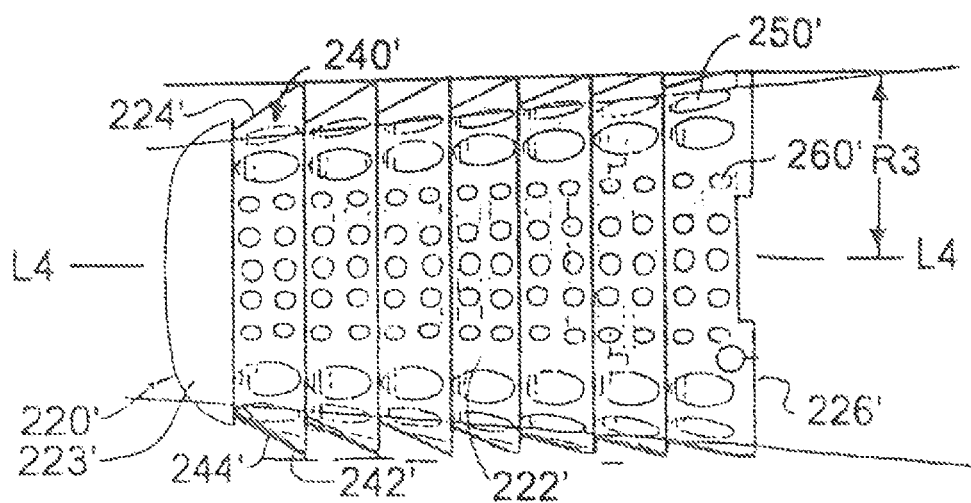

SPINAL FUSION IMPLANT

RELATED APPLICATIONS

This application is a continuation of application Ser. No. 12/798,364, filed Apr. 3, 2010, now U.S. Pat. No. 7,942,933; which is a continuation of application Ser. No. 11/085,706, filed Mar. 19, 2005, now U.S. Pat. No. 7,691,148; which is a continuation of application Ser. No. 08/484,928, filed Jun. 7, 1995, now U.S. Pat. No. 6,923,810; all of which are incorporated herein by reference.

The disclosures of U.S. Pat. Nos. 5,015,247; 5,484,437; and 6,080,155 are incorporated by reference herein.

BACKGROUND OF THE INVENTION

1. Field of the Invention

The present invention relates generally to interbody spinal fusion implants, and in particular to spinal fusion implants configured to restore and maintain two adjacent vertebrae of the spine in anatomical lordosis.

2. Description of the Related Art

Interbody spinal fusion refers to the method of achieving bony bridging between adjacent vertebrae through the disc space, the space between adjacent vertebrae normally occupied by a spinal disc. Numerous implants to facilitate such a fusion have been described by Cloward, Brantigan, and others, and are known to those skilled in the art. Generally, cylindrical implants offer the advantage of conforming to an easily prepared recipient bore spanning the disc space and penetrating into each of the adjacent vertebrae. Such a bore may be created by use of a drill. It is an anatomical fact that both the cervical spine and the lumbar spine are normally lordotic, that is convex forward. Such alignment is important to the proper functioning of the spine. Commonly, those conditions which require treatment by spinal fusion are associated with a loss of lordosis.

Therefore, there exists a need for spinal fusion implants that permit for the restoration of anatomical lordosis.

SUMMARY OF THE INVENTION

The present invention is directed to a variety of interbody spinal fusion implants having at least a partially frusto-conical configuration to achieve a desired anatomical lordosis of the spine. In the preferred embodiment, the spinal fusion implants of the present invention have an outer locus in which at least some of the points of the implant comprise a partially or fully frusto-conical shape substantially along those portions of the implant in contact with the adjacent vertebrae of the spine and have an insertion end and a trailing end. The spinal fusion implants of the present invention may be further modified so that while the upper and lower surfaces are portions of a frusto-cone, at least one side portion may be truncated to form a planar surface that is parallel to the central longitudinal axis of the implant to form straight wells. These implants may have a more tapered aspect at the insertion end of the implant to facilitate insertion. The spinal fusion implants of the present invention may be relatively solid and/or porous and/or hollow, and may have surface roughenings to promote bone ingrowth and stability.

The spinal fusion implants of the present invention may have wells extending into the material of the implant from the surface for the purpose of holding fusion promoting materials and to provide for areas of bone ingrowth fixation. These wells, or holes, may pass either into or through the implant and may or may not intersect. The spinal fusion implants of the present invention may have at least one chamber which may be in communication through at least one opening to the surface of the implant. Said chamber may have at least one access opening for loading the chamber with fusion promoting substances. The access opening may be capable of being closed with a cap or similar means. Still further, a variety of surface irregularities may be employed to increase implant stability and implant surface area, and/or for the purpose of allowing the spinal fusion implant to be inserted easily but to resist motion in the oppostion direction. The exterior of the spinal fusion implant of the present invention may have wholly or in part, a rough finish, knurling, forward facing ratchetings or other surface irregularities sufficient to achieve the purpose described.

The spinal fusion implants of the present invention offer significant advantages over the prior art implants:

1. Because the spinal fusion implants of the present invention are at least partially frusto-conical in shape, those that taper from the leading edge to the trailing edge are easy to introduce and easy to fully insert into the spinal segment to be fused.
2. The shape of the implants of the present invention is consistent with the shape of the disc, which the implants at least in part replace, wherein the front of the disc is normally taller than the back of the disc, which allows for normal lordosis. The implants of the present invention are similarly taller anteriorly than they are posteriorly.
3. The spinal fusion implants of the present invention conform to a geometric shape, which shape is readily producible at the site of fusion, to receive said spinal fusion implants.

The spinal fusion implants of the present invention can be made of any material appropriate for human implantation and having the mechanical properties sufficient to be utilized for the intended purpose of spinal fusion, including various metals such as cobalt chrome, stainless steel or titanium including its alloys, various plastics including those which are bioabsorbable, and various ceramics or combination sufficient for the intended purpose. Further, the spinal fusion implants of the present invention may be made of a solid material, a mesh-like material, a porous material and/or may comprise, wholly or in part, materials capable of directly participating in the spinal fusion process, or be loaded with, composed of, treated or coated with chemical substances such as bone, morphogenic proteins, hydroxyapatite in any of its forms, and osteogenic proteins, to make them bioactive for the purpose of stimulating spinal fusion. The implants of the present invention may be wholly or in part bioabsorbable.

OBJECTS OF THE PRESENT INVENTION

It is an object of the present invention to provide a spinal fusion implant that is easily inserted into the spine, having a tapered leading end;

It is another object of the present invention to provide a spinal fusion implant that tapers in height from one end to the other consistent with the taper of a normal spinal disc;

It is yet another object of the present invention to provide a spinal fusion implant that is capable of maintaining anatomic alignment and lordosis of two adjacent vertebrae during the spinal fusion process;

It is still another object of the present invention to provide a spinal fusion implant that is self stabilizing within the spine;

It is yet another object of the present invention to provide a spinal fusion implant that is capable of providing stability between adjacent vertebrae when inserted;

It is still another object of the present invention to provide a spinal fusion implant that is capable of participating in the fusion process by containing, being composed of, or being treated with fusion promoting substances;

It is further another object of the present invention to provide a spinal fusion implant that is capable of spading apart and supporting adjacent vertebrae during the spinal fusion process;

It is still further another object of the present invention to provide a spinal fusion implant that is consistent in use with the preservation of a uniform thickness of the subchondral vertebral bone;

It is another object of the present invention to provide a spinal fusion implant having a shape which conforms to an easily produced complementary bore at the fusion site; and It is a further object of the present invention to provide a frusto-conical spinal fusion implant which may be placed side by side adjacent to a second identical implant across the same disc space, such that the combined width of the two implants is less than sum of the individual heights of each implant.

These and other objects of the present invention will become apparent from a review of the accompanying drawings and the detailed description of the drawings.

BRIEF DESCRIPTION OF THE DRAWINGS

FIG. 3A is a side-elevational view of an alternative embodiment of the spinal fusion implant of the present invention having a frusto-conical body and a plurality of ratchetings forming a cylindrical external configuration.

DETAILED DESCRIPTION OF THE DRAWINGS

Figure 1A:
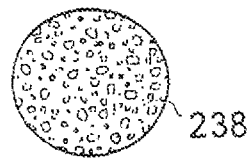
FIG. 1A is an enlarged fragmentary view along line 1A of FIG. 1 illustrating the surface configuration of the implant of FIG. 1.
Figure 1:
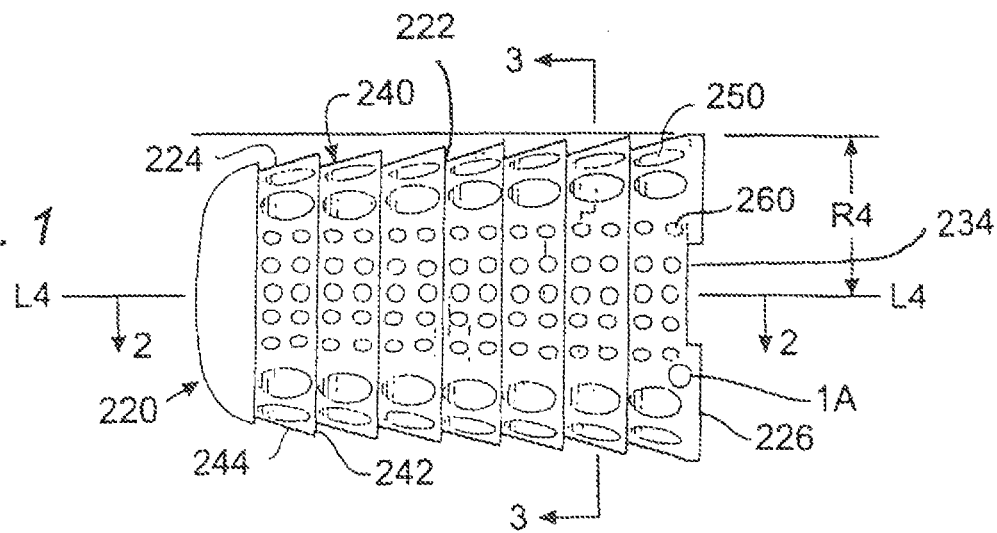
FIG. 1 is a side elevational view of an embodiment of the spinal fusion implant of the present invention having a frusto-conical body and a surface configuration comprising ratchetings for engaging bone, with wells and channels for bone ingrowth.

Referring to FIG. 1, an embodiment of the spinal fusion implant of the present invention is shown and generally referred to by the numeral 220. The implant 220 has a frusto-conical body 222 and an outer locus that is generally frusto-conical substantially along the portion of the implant 220 that is in contact with the adjacent vertebrae of the spine. The implant 220 has a surface configuration of forward facing ratchetings 240 suitable for engaging the bone of the adjacent vertebrae. Each of the plurality of ratchetings 240 has a bone engaging edge 242 and ramped portion 244. The ratchetings 240 have a radius $R_4$ measured from the central longitudinal axis $L_4$ of the implant 220 that increases from the insertion end 224 to the trailing end 226. The height of the ratchetings 240 measured from the body 222 is constant throughout the length of implant 220.

The orientation of the ratchetings 240 makes the insertion of the implant 220 easier than its removal, as the ramped portions 244 act as an inclined plane on the way in, while the bone engaging edges 242 resist motion in the opposite directions. These forward facing ratchetings 240 tend to urge the implant 220 forward until the unremoved bone of the vertebrae blocks further motion resulting in a very stable spine and implant construct.

The implant 220 has recessed slot 234 at its trailing end 226 for receiving and engaging insertion instrumentation for inserting the implant 220. The recessed slot 234 has a threaded opening 236 for threadably attaching the implant 220 to instrumentation used for inserting the implant 220.

In the preferred embodiment, the bone engaging edges 242 of the ratchetings 240 have a height at a highest point measured from the body 222 (root diameter) of the implant 220 in the range of 0.25-2.0 mm, with the preferred height being 0.4 mm for use in the cervical spine and 1.25 mm for use in the lumbar spine.

Figure 2:
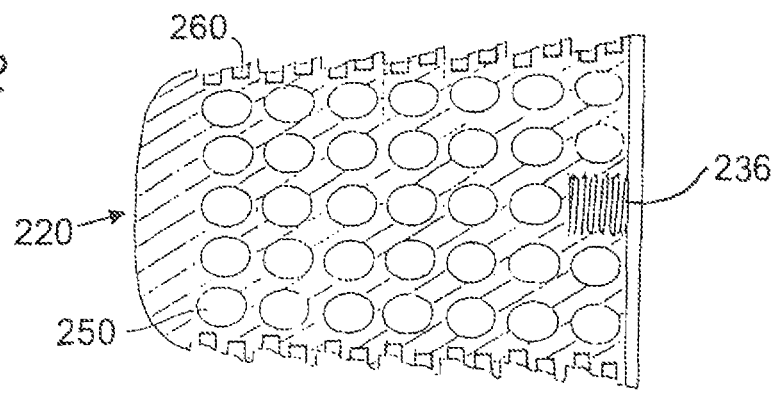
FIG. 2 is a cross sectional view along line 2--2 of the implant of FIG. 1 illustrating the channels and wells of the implant of the present invention.
Figure 3:
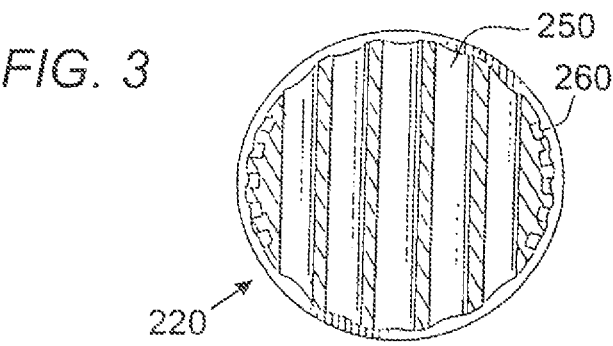
FIG. 3 is a cross sectional view along line 3--3 of the implant of FIG. 1 illustrating the channels and wells of the implant of the present invention.

Referring to FIGS. 2 and 3, cross sectional views of implant 220 are shown. The implant 220 has channels 250 passing through the implant 220 and wells 260 formed in the surface of the implant 220. The wells 260 may or may not communicate with the channels 250. In the preferred embodiment of implant 220, the channels 250 have a diameter in the range of 0.1 mm to 6 mm, with 2-3 mm being the preferred diameter. The wells 260 have a diameter in the range of 0.1 mm to 6 mm, with 1-3 mm being the preferred diameter range. It is appreciated that although the channels 250 and wells 260 are shown having a generally rounded configuration, it is within the scope of the present invention that the channels 250 and wells 260 may have any size, shape, configuration, and distribution suitable for the intended purpose.

Referring to FIG. 1A, the implant 220 has an outer surface 238 that is porous to present an irregular surface to the bone to promote bone ingrowth. The outer surface 238 is also able to hold fusion promoting materials and provides for an increased surface area to engage the bone in the fusion process and to provide further stability. It is appreciated that the outer surface 238, and/or the entire implant 220, may comprise any other porous material or roughened surface sufficient to hold fusion promoting substances and/or allow for bone ingrowth and/or engage the bone during the fusion process. The implant 220 may be further coated with bioactive fusion promoting substances including, but not limited to, hydroxyapatite compounds, osteogenic proteins and bone morphogenic proteins. The implant 220 is shown as being solid, however it is appreciated that it can be made to be substantially hollow or hollow in part.

While the implant 220 is shown as being solid, it is appreciated that the implant 220 can be hollow at least in part to provide an internal chamber for holding bone or any fusion promoting material. Such an implant could have openings to allow bone external to the implant to grow into the internal chamber. Such structure is disclosed in detail in application Ser. No. 08/390,131, now U.S. Pat. No. 5,593,409, and application Ser. No. 08/074,781, now U.S. Pat. No. 5,484,437, both of which are incorporated herein by reference.

Referring to FIG. 3A, an alternative embodiment of the implant 220 is shown and generally referred to by the numeral 220'. The implant 220' is similar in configuration to implant 220 except that the body 222' of the implant is frusto-conical in configuration and the ratchetings 240' have a radius $R_3$ measured from the longitudinal central axis $L_4$ that is constant in size from the insertion end 224' to the trailing end 226'. The ratchetings 240' each have a height measured from the body 222' that is not constant throughout the length of the implant 220' and decreases from the insertion end 224' to the trailing end 226'. In this manner, the ratchetings 240' form an external configuration of the implant 220' that is substantially cylindrical in shape, while the body 222' is frusto-conical. The insertion end of implant 220' may have a tapered portion 223' of lesser diameter to facilitate insertion of the implant 220'. The insertion end of the implant may also be larger than the trailing end where so desired.

Figure 4:
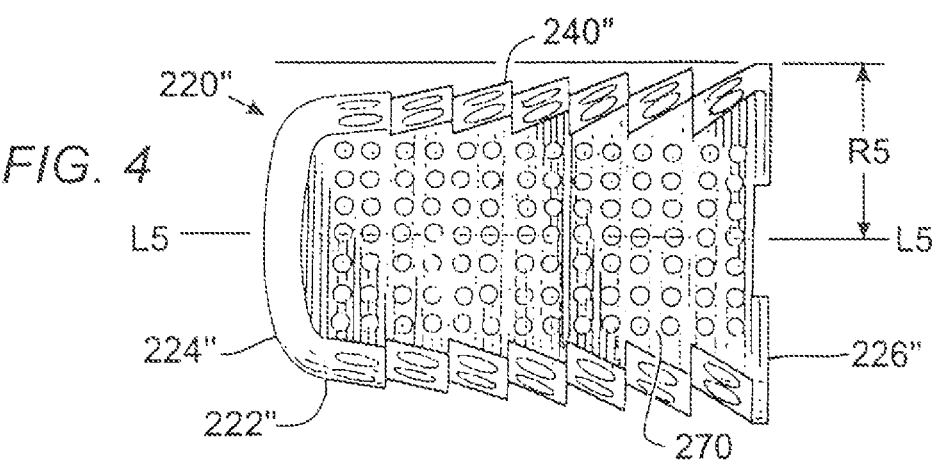
FIG. 4 is a side elevational view of an alternative embodiment of the spinal fusion implant of the present invention having truncated sides forming a planar surface parallel to the longitudinal axis of the implant and ratchetings having a radius and height that are not constant.
Figure 5:
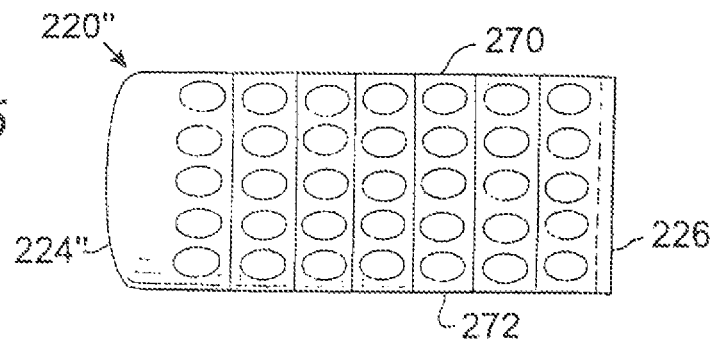
FIG. 5 is a top plan view of the spinal fusion implant shown in FIG. 4.

Referring to FIGS. 4 and 5, an alternative embodiment of the implant 220 is shown and generally referred to by the numeral 220". The implant 220" is similar in configuration to implant 220 and has ratchetings 240" having a radius $R_5$ measured from the longitudinal central axis $L_5$ that increases in size from the insertion end 224" to the trailing end 226". The ratchetings 240" each have a height measured from the body 222" that is not constant throughout the length of the implant 220". In the preferred embodiment, the ratchet radius $R_5$ and the ratchet height increase in size from the insertion end 224" to the trailing end 226".

As shown in FIG. 5, the implant 220" has truncated sides 270 and 272 forming two planar surfaces which are diametrically opposite and are parallel to the longitudinal axis $L_5$. In this manner, two implants 220" may be placed side by side with one of the sides 270 or 272 of each implant touching, such that the area of contact with the bone of the adjacent vertebrae and the ratchetings 240 is maximized. Alternatively, the implant 220" may have one truncated side.

Figure 6:
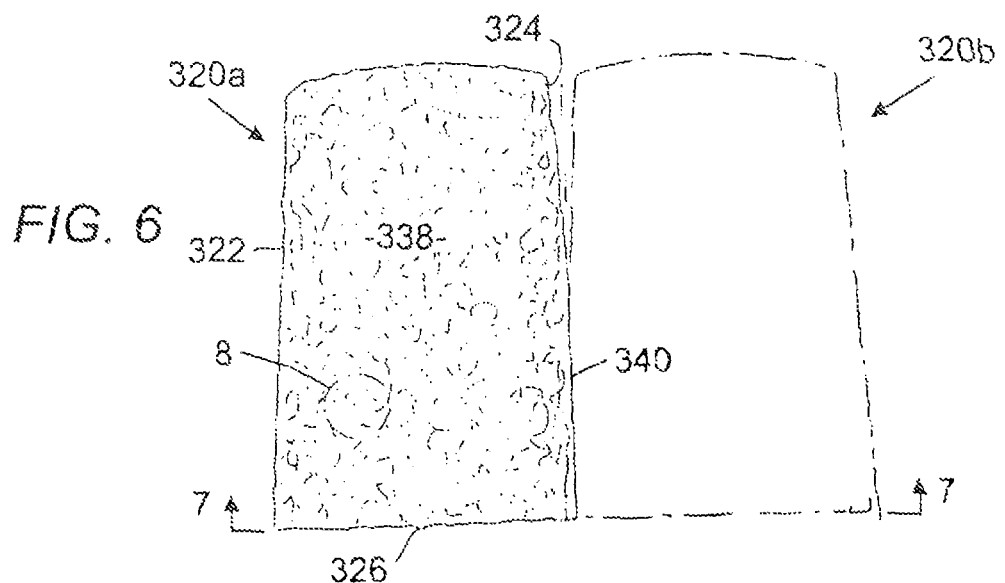
FIG. 6 is a side elevational view of an alternative embodiment of the spinal fusion implant of the present invention having a body that is made out of a fibrous mesh-like material that is partially frusto-conical with one side that is truncated shown next to an identical second implant illustrated in hidden line.
Figure 7:
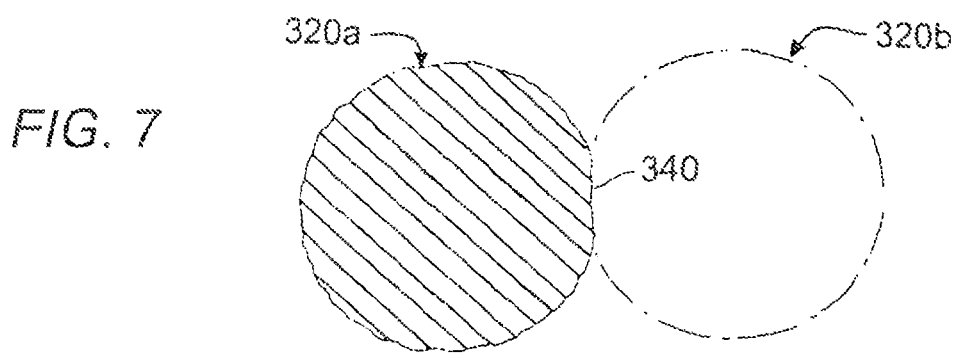
FIG. 7 is sectional view along line 7--7 of the implants of FIG. 6.
Figure 8:
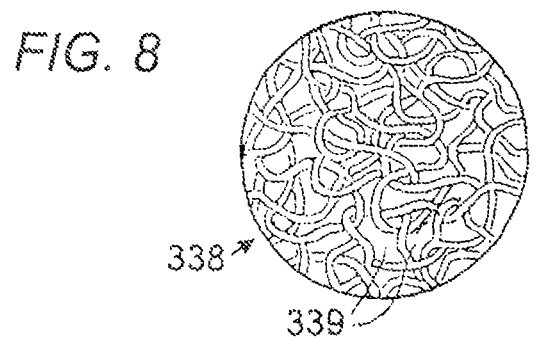
FIG. 8 is an enlarged fragmentary view along line 8 of FIG. 6 illustrating the surface configuration of the implant of FIG. 6.

Referring to FIGS. 6-8, an alternative embodiment of the spinal fusion implant of the present invention is shown and generally referred to by the numeral 320a. The implant 320a is shown placed next to a second identical implant 320b shown in hidden line. The implant 320a has a body 322 that is made of a mesh-like material comprising strands, which may be made of metal, that are pressed together and molded into a partially frusto-conical configuration substantially along the portion of the implant 320a in contact with the adjacent vertebrae of the spine. The implant 320a has an insertion end 324 and a trailing end 326 and may be made wholly or in part of a solid material and/or a porous material, and/or a mesh-like material. The implant 320a may have a surface comprising of a porous material, a mesh-like material, or have a surface that is roughened. It is appreciated that the implant 320a may be solid or may be partially hollow and include at least one internal chamber. As shown in FIG. 8, the mesh-like material comprises strands that are formed and pressed together such that interstices 339, capable of retaining fusion promoting material and for allowing for bone ingrowth, are present between the strands in at least the outer surface 338 of implant 320a.

Figure 9:
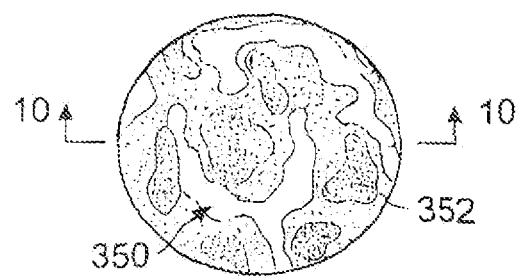
FIG. 9 is an enlarged fragmentary view along line 8 of FIG. 6 illustrating an alternative embodiment of the surface configuration of the implant of the present invention made of a cancellous material.
Figure 10:
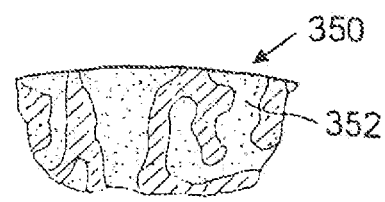
FIG. 10 is a cross sectional view along lines 10--10 of FIG. 9 illustrating the alternative embodiment of the surface configuration of the implant of the present invention made of a cancellous material.

Referring to FIGS. 9 and 10, alternatively the implant may be made of a cancellous material 350, similar in configuration to human cancellous bone, having interstices 352 such that the outer surface has a configuration as shown in FIGS. 9 and 10. As the implant may be made entirely or in part of the cancellous material 350, the interstices 352 may be present in the outer surface and/or within the entire implant to promote bone ingrowth and hold bone fusion promoting materials.

Referring again to FIG. 7, the implant 320a is partially frusto-conical, similar in shape to implant 220 but having at least one truncated side 340 that forms a planar surface parallel to the central longitudinal axis of implant 320a. The truncated side 340 allows for the placement of two implants 320a and 320b closer together when placed side by side between two adjacent vertebrae as set forth in U.S. patent application Ser. No. 08/390,131, now U.S. Pat. No. 5,593,409, incorporated herein by reference. Implant 320a may be partially threaded or may otherwise resemble any of the other embodiments herein described or that are functionally equivalent.

Figure 11:
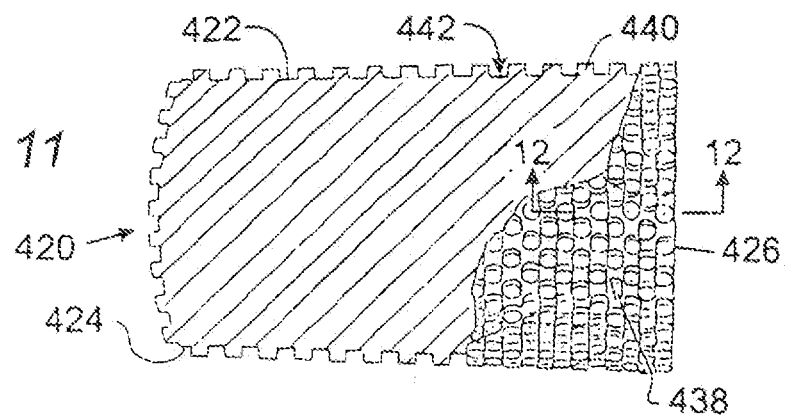
FIG. 11 is a side elevational view in partial cut-away of an alternative embodiment of the spinal fusion implant of the present invention having a body that is frusto-conical and a surface configuration comprising a plurality of spaced apart posts.

Referring to FIG. 11, a side elevational view in partial cut-away of an alternative embodiment of the implant of the present invention is shown and generally referred to by the numeral 420. The implant 420 has a body 422 that is frusto-conical in shape substantially along the portion of the implant 420 that is in contact with the adjacent vertebrae of the spine and has an insertion end 424 and a trailing end 426. The implant 420 has an outer surface 438 that is capable of receiving and holding bone, or other materials capable of participating in the fusion process and/or capable of promoting bone ingrowth. In the preferred embodiment, the surface 438 comprises a plurality of posts 440 that are spaced apart to provide a plurality of interstices 442 which are partial wells with incomplete walls capable of holding and retaining milled bone material or any artificial bone ingrowth promoting material. The implant 420 may be prepared for implantation by grouting or otherwise coating the surface 438 with the appropriate fusion promoting substances.

Figure 12:
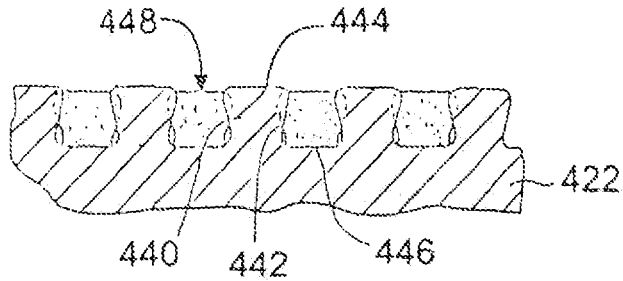
FIG. 12 is an enlarged fragmentary sectional view along lines 12-12 of FIG. 11 illustrating the surface configuration of the implant of FIG. 11.

Referring to FIG. 12, an enlarged view of the surface 438 of implant 420 is shown. In the preferred embodiment, the posts 440 have a head portion 444 of a larger diameter than the remainder of the posts 440, and each of the interstices 442 is the reverse configuration of the posts 444, having a bottom 446 that is wider than the entrance 448 to the interstices 442. Such a configuration of the posts 440 and interstices 442 aids in the retention of bone material in the surface 438 of the implant 420 and further assists in the locking of the implant 420 into the bone fusion mass created from the bone ingrowth. As the bone ingrowth at the bottom 446 of the interstices 442 is wider than the entrance 448, the bone ingrowth cannot exit from the entrance 448 and is locked within the interstice 442. The surface 438 of the implant 420 provides for an improvement in the available amount of surface area which may be still further increased by rough finishing, flocking or otherwise producing a non-smooth surface.

In the preferred embodiment, the posts 440 have a maximum diameter in the range of approximately 0.1-2 mm and a height of approximately 0.1-2 mm and are spaced apart a distance of approximately 0.1-2 mm such that the interstices 442 have a Width in the range of approximately 0.1 to 2 mm. The post sizes, shapes, and distributions may be varied within the same implant.

While the present invention has been described in detail with regards to the preferred embodiments, it is appreciated that other variations of the present invention may be devised which do not depart from the inventive concept Of the present invention. In particular, it is appreciated that the various teachings described in regards to the specific embodiments herein may be combined in a variety of ways such that the features are not limited to the specific embodiments described above.

Each of the features disclosed in the various embodiments and their functional equivalents may be combined in any combination sufficient to achieve the purposes of the present invention as described herein.

What is claimed is:

1. An interbody spinal fusion implant for insertion across the surgically corrected height of a disc space between two adjacent vertebral bodies of a human spine, said implant comprising:

a leading end for insertion first into the disc space, a trailing end opposite said leading end, a length between said ends, a mid-longitudinal axis passing through said leading and trailing ends, and a cross-sectional profile in a plane that is proximate said trailing end and is perpendicular to the mid-longitudinal axis, the cross-sectional profile including two generally arcuate portions and two generally linear portions, said trailing end including a threaded bore with a central longitudinal axis that coincides with the mid-longitudinal axis of said implant;

opposed upper and lower portions adapted to contact the adjacent vertebral bodies when implanted in the spine, said opposed upper and lower portions of said implant including at least one opening in communication with one another for permitting for the growth of bone from vertebral body to vertebral body through said implant; and bone engaging projections for engaging said implant to the adjacent vertebral bodies, said bone engaging projections extending from at least a portion of said opposed upper and lower portions, each of said bone engaging projections having a forward-facing facet directed at least in part toward said leading end, each of said forward-facing facets having a slope relative to the mid-longitudinal axis, the slope of said forward-facing facets decreasing from one of said ends toward another of said ends.

2. The implant of claim 1, wherein said implant includes two opposed planar portions, said planar portions extending along at least a portion of the length.

3. The implant of claim 1, wherein said upper and lower portions form at least a portion of a cylinder.

4. The implant of claim 1, wherein said bone engaging projections include a plurality of ratchetings.

5. The implant of claim 1, wherein said implant has a hollow interior and an access opening for accessing said hollow interior.

6. The implant of claim 5, further comprising a cap for closing said access opening.

7. The implant of claim 1, wherein said trailing end is adapted to engage instrumentation for the insertion of said implant.

8. The implant of claim 1, wherein said implant is configured to be placed in close proximity in a side by side alignment to a second implant.

9. The implant of claim 1, wherein said upper and lower portions form at least a portion of a cone.

10. The implant of claim 1, wherein said upper and lower portions are at least in part arcuate.

11. The implant of claim 1, wherein said upper and lower portions are at least in part arcuate from side to side along at least a portion of the length of said implant.

12. The implant of claim 1, wherein said upper and lower portions are angled relative to one another so as to maintain an angulation of the adjacent vertebral bodies relative to one another.

13. The implant of claim 12, wherein said upper and lower portions are at least in part arcuate.

14. The implant of claim 1, wherein said upper and lower portions each include a portion that is an arc of the same circle.

15. The implant of claim 1, wherein, each of said bone engaging projections have a rearward-facing portion directed at least in part toward, said trailing end.

16. The implant of claim 1, wherein each of said bone engaging projections have a rearward-facing portion directed at least in part toward said trailing end, said rearward-facing portions having the same slope.

17. The implant of claim 1, wherein said bone engaging projections are positioned one in front of another along the majority of the length of said implant.

18. The implant of claim 1, wherein said bone engaging projections are immediately adjacent one another along the majority of the length of said implant.

19. The implant of claim 1, in combination with a fusion promoting substance.

20. The implant of claim 1, wherein the slope of said forward-facing facets of said bone engaging projections relative to the mid-longitudinal axis decreases from said leading end toward said trailing end.

* * * * *

UNITED STATES PATENT AND TRADEMARK OFFICE
CERTIFICATE OF CORRECTION

| | | |
|---|---|---|
| PATENT NO. | : 8,409,292 B2 | Page 1 of 1 |
| APPLICATION NO. | : 13/109791 | |
| DATED | : April 2, 2013 | |
| INVENTOR(S) | : Gary Karlin Michelson | |

It is certified that error appears in the above-identified patent and that said Letters Patent is hereby corrected as shown below:

Title Page 1, Item (56) References Cited, U.S. Patent Documents:
Column 2, line 3: change "Moreira" to -- De G. Moreira --.

Title Page 3, Item (56) References Cited, Other Publications:
Column 2, line 35: change "H.V.;" to -- H.V.; --.

Title Page 4, Item (56) References Cited, Other Publications:
Column 2, line 27: change "Encephalomeningaceles" to -- Encephalomeningoceles --.

In the Claims:
Column 8, Claim 15:
Line 35: change "wherein, each" to -- wherein each --; and
Line 37: change "toward, said" to -- toward said --.

Signed and Sealed this
Eighteenth Day of February, 2014

Michelle K. Lee
*Deputy Director of the United States Patent and Trademark Office*